United States Patent [19]

Luksza

[11] Patent Number: 4,810,796

[45] Date of Patent: Mar. 7, 1989

[54] PREPARATION OF PYRIDINOL CARBAMATE

[75] Inventor: Michael Luksza, Bad Duerkheim, Fed. Rep. of Germany

[73] Assignee: BASF Aktiengesellschaft, Ludwigshafen, Fed. Rep. of Germany

[21] Appl. No.: 14,446

[22] Filed: Feb. 13, 1987

[30] Foreign Application Priority Data

Feb. 15, 1986 [DE] Fed. Rep. of Germany ....... 3604873

[51] Int. Cl.$^4$ ............................................. C07D 213/75
[52] U.S. Cl. .................................... 546/335; 546/331
[58] Field of Search ........................ 546/291, 331, 335

[56] References Cited

U.S. PATENT DOCUMENTS 3,467,663  9/1969  Inoue et al. ........................ 546/265

FOREIGN PATENT DOCUMENTS 417812  8/1973  Spain ..................................... 546/335

OTHER PUBLICATIONS

Nachr. Chem. Tech. Lab., vol. 33 (1985), Nr. 7, pp. 590-591.
Arch. Pharm. 310, 759 (1977).

*Primary Examiner*—Alan L. Rotman
*Attorney, Agent, or Firm*—Keil & Weinkauf

[57] ABSTRACT

Pyridinol carbamate is prepared by a process in which a carbamate of the formula $$H_3C-NH-CO-O-R$$

where R is methyl, ethyl, n-propyl, isopropyl, n-butyl, isobutyl or tert.-butyl, is reacted with 2,6-bis-(hydroxymethyl)-pyridine in the presence of a transesterification catalyst of the Lewis acid type in the liquid phase at elevated temperatures.

7 Claims, No Drawings

PREPARATION OF PYRIDINOL CARBAMATE

The present invention relates to a process for the preparation of pyridinol carbamate (2,6-bis-(hydroxymethyl)-pyridine 2,6-bis-(N-methylcarbamate)).

Pyridinol carbamate is a bradykinin antagonist which has an antiarteriosclerotic action (cf. Ehrhart and Ruschig; Arzneimittel II, page 435, Verlag Chemie Weinheim 1972) and is obtainable by reacting 2,6-bis-(hydroxymethyl)-pyridine with methyl isocyanate. FR-A-1 396 624 discloses the reaction of these two substances in pyridine. After a total reaction time of 15 hours (12 hours at room temperature and 3 hours at the boil), the desired product is obtained in virtually quantitative yield. According to T. Szén and A. Szöllosy (Arch. Pharm. 310 (1977), 759–762), the mono- and diallophanates are formed as byproducts (2–5%) in the reaction of the pyridinol carbamate with excess methyl isocyanate, or trismethyl isocyanurate is formed as a degradation product.

An important disadvantage of this process is the use of methyl isocyanate, whose preparation from phosgene and methylamine and whose handling involves substantial risks owing to the high toxicities (cf. Nachr. Chem. Techn. Lab. 33 (1985), No. 7, 590).

ES-A-417 812 describes the transesterification of 2,6-bis-(hydroxymethyl)-pyridine with ethyl carbamate ($H_3CNHCOOC_2H_5$) in the presence of Al-(O—iso—$C_3H_7$)$_3$ in xylene as the solvent to give pyridinol carbamate. Our own investigations have shown that, under the conditions stated in the patent (cf. lines 25 to 30, page 2; lines 1 to 5, page 3), the design product can only be obtained in traces.

We have found a process by means of which pyridinol carbamate can be prepared in good yield from starting compounds which are simple to handle and not very toxic.

The present invention relates to a process for the preparation of pyridinol carbamate, wherein a carbamate of the formula

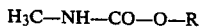

$H_3C-NH-CO-O-R$ where R is methyl, ethyl, n-propyl, isopropyl, n-butyl, isobutyl or tert.-butyl, is reacted with 2,6-bis-(hydroxymethyl)-pyridine in the presence of a transesterification catalyst of the Lewis acid type in the liquid phase at elevated temperatures, the transesterification being carried out in the absence of a solvent or in an inert solvent, with the exception of xylene.

In a preferred embodiment, transesterification is effected at from 130° to 180° C., in particular from 150° to 170° C.

The novel process is carried out in the presence of a Lewis acid transesterification catalyst. Examples are aluminum alcoholates, tin tetrachloride, organo-tin compounds, titanium alcoholates, zirconium alcoholates and acidic zeolites. Tin tetrachloride, aluminum triisopropylate and acidic zeolites are preferably used. Tin tetrachloride and aluminum triisopropylate are used in an amount of, preferably, from 1.0 to 10 mol%, and acidic zeolites are employed in an amount of, preferably, from 3 to 6 percent by weight.

The reaction is advantageously carried out under from 0.02 to 1 bar, preferably under atmospheric pressure.

The molar ratio of the two reactants 2,6-bis-(hydroxymethyl)-pyridine to carbamate is preferably from 1:2.5 to 1:8, particularly preferably from 1:2.5 to 1:4.0.

The novel process can be carried out in the absence of a solvent but is preferably effected in the presence of an inert solvent, with the exception of xylene. Particularly preferably used solvents are excess carbamate or 1,2-dichlorobenzene. However, other inert organic, aliphatic or aromatic solvents having a boiling point of from 150° to 250° C. are also suitable, xylene being the only solvent which does not give the desired result. The reason for this is not known. Examples of other suitable solvents are n-nonane, decahydronaphthalene, n-butylcyclohexane, n-undecane, n-dodecane, isopropylbenzene, 1,3-diethylbenzene, indene, tetralin, anisole, phenyl n-propyl ketone, benzophenone, acetophenone, N-methylformamide, N,N-dimethylformamide, N,N-dimethylaniline, N,N-dimethyl-2-methylaniline, 4-methoxytoluene, hexamethylphosphorotriamide, dimethyl sulfoxide, 2-ethylpyridine, quinoline, nitrocyclohexane, nitrobenzene, 2-nitrotoluene, 2,4-dimethyl-1-nitrobenzene, o-toluenecarbonitrile, p-toluenecarbonitrile, phenylacetonitrile, diethylene glycol dimethyl ether, dimethylpropyleneurea and sulfolane.

The process according to the invention is advantageously carried out as follows: a mixture of the reactants in the stated molar ratio is heated to elevated temperature. The alcohol liberated is removed from the reaction equilibrium via a condenser thermostatted at a temperature which is about 5° higher than the boiling point of the alcohol to be eliminated. The reaction is complete after from 4 to 12 hours.

After the removal of excess carbamate, and where relevant the solvent and undesirable byproducts, such as trimethyl isocyanurate and dimethylurea (these result from partial thermal decomposition of the carbamate or of the pyridine dicarbamate), the desired product is obtained in a yield of 40–98%.

For further purification, it is advisable to dissolve the pyridinol dicarbamate (I) in water and concentrated hydrochloric acid, and to extract the solution with xylene, toluene or methylene chloride. The aqueous phase is then neutralized with dilute sodium carbonate solution, and the product is isolated by filtering it off under suction.

The particular advantages of the novel process are that the synthesis of the pyridinol dicarbamate is isocyanate-free and therefore presents no problems from the point of view of safety. Moreover, the carbamates used are obtainable by a novel, phosgene-free electrooxidation, starting from methylformamide (see German Patent Application No. P 35 29 531.7). In general, the carbamates, the catalyst systems and the reaction procedure can be varied over a broader range than hitherto.

Byproducts occur only in small amounts and are essentially attributable to the decomposition of the carbamate. Unconverted 2,6-bis-(hydroxymethyl)-pyridine can be recovered by extraction and recycled to the reaction.

The Examples which follow illustrate the invention.

EXAMPLE 1

A solution of 35 g (0.25 mole) of 2,6-bis-(hydroxymethyl)-pyridine in 178 g (2.0 moles) of methyl N-methylcarbamate and 6.5 g (0.025 mole) of tin tetrachloride were heated to 166° C., methanol liberated being distilled off slowly via a column thermostatted at 70° C. After 12 hours, the theoretical amount of alcohol had passed over. The mixture was evaporaed to dryness under reduced pressure, the residue was taken up in hot acetone, insoluble material was filtered off from the hot solution, the latter was then cooled to 0° C. in an ice bath, and precipitated pyridinol carbamate was filtered off. The yield was 41 g (65%).

EXAMPLE 2

A solution of 35 g (0.25 mole) of 2,6-bis-(hydroxymethyl)-pyridine in 178 g (2.0 moles) of methyl N-methylcarbamate and 2 g of an acidic aluminum zeolite were heated to 166° C., methanol liberated being distilled off slowly via a column thermostatted at 70° C. After 12 hours, the theoretical amount of alcohol had passed over. The mixture was evaporated to dryness under reduced pressure, the residue was taken up in hot acetone, insoluble material was filtered off from the hot solution, the latter was then cooled to 0° C. in an ice bath, and precipitated pyridinol carbamate was filtered off. The yield was 26 g (41%).

EXAMPLE 3

A solution of 17.5 g (0.125 mole) of 2,6-bis(hydroxymethyl)-pyridine in 77 g (0.75 mole) of ethyl N-ethylcarbamate and 312 g (0.0125 mole) of tin tetrachloride were heated to 166° C., the ethanol liberated being distilled off via a column thermostatted at 85° C. After 12 hours, the theoretical amount of alcohol passed over. The mixture was evaporaed to dryness under reduced pressure, the residue was taken up in hot acetone, insoluble material was filtered off from the hot solution, the latter was then cooled to 0° C. in an ice bath, and precipitated pyridinol carbamate was filtered off. The yield was 13 g (41%).

EXAMPLE 4

13.4 g (0.15 mole) of methyl N-methylcarbamate in 10 ml of 1,2-dichlorobenzene were added dropwise, at 165° C. in the course of 2 hours, to a solution of 8.34 g (0.06 mole) of 2,6-bis-(hydroxymethyl)-pyridine and 1.22 g (0.006 mole) of aluminum triisopropylate in 40 ml of the same solvent, methanol liberated being distilled off via a column thermostatted at 70° C. After 3 hours, the theoretical amount of alcohol had passed over. The mixture was evaporated to dryness under reduced pressure, and the remaining residue was suspended in water, filtered off and dried. The yield was 15.2 g (98%).

EXAMPLE 5

51.5 g (0.5 mole) of ethyl N-methylcarbamate in 50 ml of dichlorobenzene were added dropwise, at 165° C. in the course of 2 hours, to a solution of 8.75 g (0.06 mole) of 2,6-bis-(hydroxymethyl)-pyridine and 1.27 g (0.006 mole) of aluminum triisopropylate in 50 ml of dichlorobenzene, ethanol liberated being distilled off via a column thermostatted at 85° C. After 7 hours, the theoretical amount of alcohol had passed over. The mixture was evaporated to dryness under reduced pressure, and the remaining residue was suspended in water, filtered off and dried. The yield was 13.2 g (87%).

We claim:

1. A process for the preparation of pyridinol carbamate, wherein a carbamate of the formula

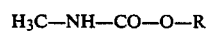

$$H_3C-NH-CO-O-R$$

where R is methyl, ethyl, n-propyl, isopropyl, n-butyl, isobutyl or tert.-butyl, is reacted with 2,6-bis-(hydroxymethyl)-pyridine in the presence of a titanium alcoholate, a zirconium alcoholate or tin tetrachloride in the liquid phase at elevated temperatures, the transesterification being carried out in the absence of a solvent or in an inert solvent, with the exception of xylene.

2. The process of claim 1, wherein the transesterification catalyst used is tin tetrachloride.

3. The process of claim 1, wherein the transesterification is carried out at from 130° to 180° C.

4. The process of claim 1, wherein the reaction is carried out under from 0.02 to 1 bar.

5. The process of claim 1, wherein the transesterification is carried out in excess carbamate as the solvent.

6. The process of claim 1, wherein 1,2-dichlorobenzene is used as the solvent.

7. The process of claim 1, wherein the molar ratio of 2,6-bis-(hydroxymethyl)-pyridine to carbamate is from 1:2.5 to 1:8.

* * * * *